United States Patent
Rathjen et al.

(10) Patent No.: US 8,414,124 B2
(45) Date of Patent: Apr. 9, 2013

(54) DEVICE AND METHOD FOR MEASURING A CORNEA

(75) Inventors: Christian Rathjen, Bremen (DE); Roger Cattin, Orpund (CH); Christoph Meier, Nidau (CH)

(73) Assignee: SIS AG, Surgical Instrument Systems (CH)

( * ) Notice: Subject to any disclaimer, the term of this patent is extended or adjusted under 35 U.S.C. 154(b) by 0 days.

(21) Appl. No.: 12/903,378

(22) Filed: Oct. 13, 2010

(65) Prior Publication Data

US 2011/0090459 A1   Apr. 21, 2011

Related U.S. Application Data

(60) Provisional application No. 61/253,545, filed on Oct. 21, 2009.

(51) Int. Cl.
*A61B 3/10* (2006.01)
*A61B 3/00* (2006.01)

(52) U.S. Cl.
USPC ............ 351/212; 351/200; 351/211; 351/221

(58) Field of Classification Search .................. 351/212, 351/200, 211, 205, 218, 221
See application file for complete search history.

(56) References Cited

U.S. PATENT DOCUMENTS

| | | | |
|---|---|---|---|
| 5,054,907 A | 10/1991 | Sklar et al. | |
| 5,116,115 A | 5/1992 | Lange et al. | |
| 5,194,882 A * | 3/1993 | Penney | 351/212 |
| 5,307,097 A * | 4/1994 | Baker | 351/212 |
| 5,592,246 A | 1/1997 | Kuhn et al. | 351/212 |
| 5,909,270 A * | 6/1999 | Moser et al. | 351/212 |
| 2003/0236516 A1* | 12/2003 | Okamoto et al. | 606/5 |
| 2004/0027537 A1* | 2/2004 | Sarver | 351/212 |
| 2006/0028619 A1* | 2/2006 | Fujieda et al. | 351/246 |

FOREIGN PATENT DOCUMENTS

| | | |
|---|---|---|
| DE | 4007502 | 9/1991 |
| DE | 102007018048 | 10/2008 |
| EP | 0445618 | 9/1991 |

* cited by examiner

*Primary Examiner* — Dawayne A Pinkney
(74) *Attorney, Agent, or Firm* — Ostrolenk Faber LLP

(57) ABSTRACT

In order to measure a cornea with the aid of a projection (S11) of a two-dimensional reference pattern onto the cornea and of a detection (S12) of the reflection pattern reflected by the cornea by virtue of the reference pattern, a plurality of different reflection images of one or more reflection patterns reflected by the cornea are stored (S13). For points on the cornea a phase value of the reflection pattern is respectively calculated on the basis of intensities respectively measured in the stored reflection images at a pixel corresponding to the relevant point. At least one measured geometrical value of the cornea is calculated (S2) on the basis of the calculated phase value. The measurement of the cornea on the basis of a plurality of different reflection images of one or more reflection patterns reflected by the cornea enables a continuous measurement of the cornea in which corresponding pixels are acquired and evaluated for each point on the cornea.

2 Claims, 7 Drawing Sheets

DEVICE AND METHOD FOR MEASURING A CORNEA

CROSS-REFERENCE TO RELATED APPLICATIONS

This application claims benefit of and priority to U.S. Provisional Patent Application No. 61/253,545 filed Oct. 21, 2009, the entire contents of which are hereby incorporated by reference herein.

BACKGROUND

1. Field of the Disclosure

The present invention relates to a device and a method for measuring a cornea. The present invention relates, in particular, to an ophthalmological device and an ophthalmological method in the case of which, for the purpose of measuring the cornea, a two-dimensional reference pattern is projected onto the cornea and a reflection pattern reflected by the cornea by virtue of the reference pattern is acquired.

2. Related Art

Keratometers (or ophthalmometers) are used to measure the surface curvature of the cornea and determine the corneal profiles. In this case, the reflection of an illuminated reference object on the cornea is acquired, and on this basis the curvature of the reflecting corneal surface is determined. In known videokeratometers, a number of concentric rings are projected onto the cornea. In this procedure, it is preferred to respectively provide or illuminate a diffusely scattering body (screen) with a pattern (for example placido pattern) which is reflected by the eye and recorded by a camera located mostly on the visual axis of the eye. In addition to radial ring patterns, there are also other discrete patterns with binary light/dark structures such as, for example, two-dimensional chessboard patterns. Proceeding from the deformation of the rings on the cornea together with additional assumptions relating to the distance of the eye, that is to say relating to the location of the reflection on the cornea, a determination is made of the surface inclination of the cornea, which enables conclusions to be drawn on the refractive power of the cornea. On the basis of an expected geometrical configuration (shape) of the eye, it is also possible to determine a three-dimensional form of the cornea by integrating the radial surface inclination. By virtue of the low number of the radial interpolation points, that is to say the low number of rings or light/dark transitions (typically between fifteen and twenty rings), these measurement methods or measuring instruments are not very accurate and are affected by errors because of their limited radial resolution.

In order to improve the accuracy and the measurement range, U.S. Pat. No. 5,953,100 proposes the use of a plurality of cameras which detect reflections at the eye from various perspectives. However, because of the specular reflection of the eye a corresponding object point of the eye cannot be made out in the views of the camera (that is to say a triangulation is impossible). Consequently, each image of a camera view must be evaluated per se, and the data must be merged in a concluding step. Such methods raise the accuracy only conditionally. The number of the measuring points rises maximally in proportion to the number of cameras used.

In order to determine the corneal topography in accordance with the above method, patent specification U.S. Pat. No. 6,926,408 proposes a continuous two-dimensional pattern which uses a sinusoidal radial intensity profile and a sinusoidal angle-dependent colour profile. The pattern is generated either as a flat shape and fitted on a translucent conical shape, or the colours are applied directly to a suitable surface. The patient is positioned with his eye in front of the two-dimensional pattern, and a CCD (Charged Coupled Device) camera is used to detect the reflection pattern reflected on the cornea. In order to determine the corneal topography, the pixels of the acquired reflection pattern are respectively correlated with the corresponding reflection points on the cornea. Using a continuous reference pattern increases the number of potential measuring points by comparison with the discrete patterns mentioned at the beginning, and this allows an improvement in measuring accuracy. For a more robust image processing, U.S. Pat. No. 6,926,408 proposes the application of bandpass filters, but this reduces the resolution since, depending on the filter (in particular, on its centre frequency and bandwidth), it is respectively only filtered-out parts of the acquired reflection pattern which are evaluated, and these have a lower resolution than the unfiltered reflection pattern. Bandpass filters function better the more continuous the signal and the smaller the frequency modulation. These conditions do not obtain on the eye because of the patient-dependent variability, that is to say the strong distortion of the ring pattern, and interrupted rings (for example by eyelashes). In other words, although the use of a continuous reference pattern increases the resolution by comparison with discrete patterns, the application of bandpass filters to the corresponding reflection pattern does not lead to a continuous measurement which measures each pixel per se. Because of the slight advantages of the abovenamed practical limitations, methods with continuous patterns have not yet reached product maturity. Methods which measure each pixel per se and thus attain a maximum local resolution or number of measuring points, which lies an order of magnitude above previous methods, do not exist at present.

SUMMARY

It is an object of the present invention to propose a device and a method which, in order to measure the cornea, project a two-dimensional reference pattern onto the cornea, acquire a reflection pattern reflected by the cornea by virtue of the reference pattern, and which overcome at least certain disadvantages of the prior art. In particular, it is an object of the present invention to propose an ophthalmological device and an ophthalmological method which project a two-dimensional reference pattern onto the cornea, detect a reflection pattern reflected by the cornea by virtue of the reference pattern, and enable continuous measurement of the cornea.

In accordance with the present invention, these aims are reached, in particular, by the elements of the independent claims. Further advantageous embodiments emerge, furthermore, from the dependent claims and the description.

The abovenamed aims are reached by the present invention particularly by virtue of the fact that in an ophthalmological method and in an ophthalmological device for executing the method, in which for the purpose of measuring the cornea a two-dimensional reference pattern is projected onto the cornea and a reflection pattern reflected by the cornea by virtue of the reference pattern is acquired, a plurality of different reflection images of one or more reflection patterns reflected by the cornea are stored, and at least one measured geometrical value of the cornea is determined on the basis of the plurality of different reflection images stored. The measurement of the cornea is therefore performed on the basis of a plurality of different reflection images which are respectively detected from the same perspective of one or more reflection patterns reflected by the cornea.

A periodic reference pattern, for example with a radially running period, is preferably generated.

In one variant, the periodic reference pattern is generated with a variable period.

The reference patterns are generated, for example, by modulation of at least one physical optical parameter, such as light intensity, light polarization and/or light wavelength.

The two-dimensional reference pattern is, for example, projected onto the cornea with the aid of an active display, in particular an LCD display, or onto a passive screen with the aid of a projector (spatial light modulator), it being possible for this projection to be performed from in front or, in the case of a screen of translucent configuration, from the rear. The expression "projection of the two-dimensional reference pattern onto the cornea" is intended also to encompass the ideas both of the projection by means of the active display and the emission via the passive screen or the spatial light modulator.

The measurement of the cornea on the basis of a plurality of different reflection images of one or more reflection patterns reflected by the cornea has, in particular, the advantage of allowing continuous measurement of the cornea, corresponding pixels being acquired for each point on the cornea and evaluated, and this, in comparison with known measurement methods, allows a substantially higher resolution and higher number of measuring points in the measurement of the cornea.

For points on the cornea a phase value of the reflection pattern is preferably respectively calculated on the basis of intensities respectively measured in the stored reflection images at the corresponding pixel, and the at least one measured geometrical value of the cornea is determined on the basis of the phase value. By way of example, for points on the cornea the phase value of the reflection pattern is respectively calculated on the basis of the reflection images at the relevant point by evaluating the equation below $$I(x',y')=I_0(x',y')\{1+sm(x',y')\cos[\phi(x',y')]\},$$

$I(x',y')$ being a measured intensity at a pixel corresponding to the relevant point with the coordinates $x',y'$, $I_0(x',y')$ being a background intensity (sum composed of mean illumination value of reference pattern and background light) at the pixel, $sm(x',y')$ being a signal modulation at the pixel, and $\phi(x',y')$ being the phase value at the pixel and thus at the relevant point on the cornea.

In one design variant, a plurality of mutually shifted continuous, two-dimensional reference patterns are generated for the respective projection onto the cornea, and in each case a reflection image of reflection patterns reflected by the cornea by virtue of the shifted reference pattern is stored. The plurality of mutually shifted reference patterns are preferably generated by phase shifting of a periodic basic reference pattern, and in each case a reflection image of reflection patterns reflected by the cornea by virtue of the phase-shifted reference patterns is stored. The generation of a plurality of (phase-) shifted reference patterns and the acquisition of the corresponding reflection images allows sequential measurement of the cornea with the aid of a simple image acquisition system.

In a further design variant, the plurality of different reflection images are produced from the same reflection pattern reflected by the cornea by virtue of a continuous, two-dimensional reference pattern, and stored. The two-dimensional reference pattern is generated, for example, from two mutually phase-shifted periodic basic reference patterns respectively having a different colour, and the reflection images corresponding to the phase-shifted basic reference patterns are produced by colour filtering from the reflection pattern. In the variant having basic reference patterns of different colour, a plurality of mutually shifted (for example continuous) two-dimensional reference patterns of different colour are simultaneously projected or emitted onto the cornea. In another variant, the two-dimensional reference pattern is generated with pattern points of different polarization, and the reflection images are produced by polarization filtering from the reflection pattern. The generation of a reference pattern and the production of a plurality of reflection images based thereon allows measurement of the cornea with the aid of a single image projection step which does not influence the measuring accuracy by eye movements.

In a further design variant, two reference patterns phase-shifted by 180° relative to one another are generated, and two reflection images of the reflection patterns reflected by the cornea by virtue of the two phase-shifted reference patterns are stored. The background intensity and the signal modulation are calculated on the basis of the two reflection images for the cornea. The background intensity is, for example, calculated on the basis of an addition of the two reflection images, and the signal modulation is, for example, calculated on the basis of a subtraction of the two reflection images, the added or subtracted values respectively being halved. The separate determination of background intensity and signal modulation enables a subsequent measurement of the cornea which manages with just one image projection step, and therefore does not influence, or only slightly influences, the measuring accuracy by eye movements.

BRIEF DESCRIPTION OF THE DRAWINGS

A design of the present invention is described below with the aid of an example. The example of the design is illustrated by the following attached figures.

DETAILED DESCRIPTION OF THE EMBODIMENTS

Figure 1:
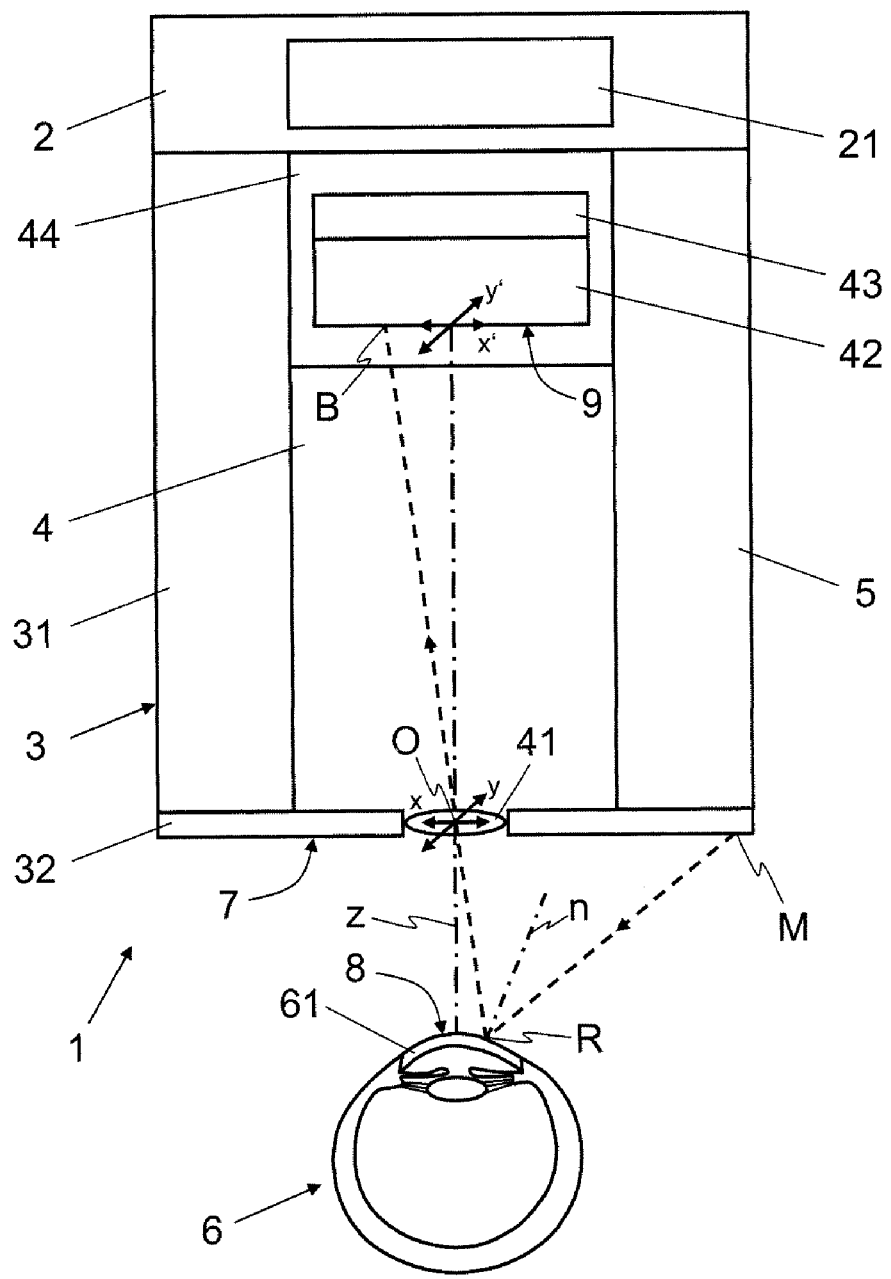
FIG. 1 shows a block diagram which illustrates an ophthalmological device for measuring a cornea which is illustrated diagrammatically in cross section.

In FIG. 1, the reference 1 relates to an ophthalmological device for measuring a cornea 61, in particular a cornea of a human eye 6.

As is illustrated diagrammatically in FIG. 1, the ophthalmological device 1 comprises a processing module 2, a reference pattern system 3, an image acquisition system 4 and an output module 5.

The processing module 2 comprises one or more computers having one or more processors, data and program memories, as well as a control module 21.

The reference pattern system 3 comprises a reference pattern generator 31 for generating two-dimensional reference patterns 7, and a reference pattern projector 32 for projecting and/or emitting the generated reference pattern 7 onto the cornea 61. The reference pattern projector 32 comprises an active display, for example an LCD (Liquid Crystal Display) display or an LED (Light Emitting Diode) display. In an alternative design variant, the reference pattern projector 32 comprises a passive screen and a projector for projecting the reference patterns onto this screen. In one variant, the active or passive display screen is of concave design, for example in the shape of a dome, in the shape of a funnel, or parabolically or ellipsoidally concave.

The image acquisition system 4 comprises an optical imaging device 41, an image converter 42, an image memory 43 and an extraction module 44. The image converter 42 comprises, for example, a CCD (Charge Coupled Device) sensor. The optical imaging device 41 comprises one or more optical lenses. The imaging device 41 is set up to image onto the image converter 42 a reflection pattern 8 which is specularly reflected by the cornea 61 by virtue of a projector/emitted reference pattern 7. In this case, a pattern point M of the reference pattern 7 is specularly reflected on the cornea 61 at the reflection point R of the reflection pattern 8 and imaged onto the pixel B of the reflection image 9 by the imaging device 41 in a focused fashion in the image converter 42. Since specular imaging is involved, only a virtual image located behind the corner 61 is present. The reflection images 9 of the reflection patterns 8 reflected by the cornea 61 and acquired in the image converter 42 are stored in the image memory 43 for further processing.

The control module 21, the reference pattern generator 31 and the extraction module 44 are functional modules which are, by way of example, designed as programmed software modules which comprise program code for controlling a processor (of the processing module 2) in such a way that the processor executes the functions described below. The person skilled in the art will understand that the functional modules can be designed in one variant completely or partially with the aid of hardware components. In particular, the extraction module 44 can comprise optical elements for the optical execution of image processing steps which, for example, are upstream of the image converter 42 or integrated in the image converter 42. The functions of the extraction module 44, which are described in more detail later, can therefore be performed entirely or in a distributed fashion upstream of the image converter 42, in the image converter 42 and/or in a fashion based on the stored reflection images 9 (downstream of the function of the image converter 42).

Figure 7A:
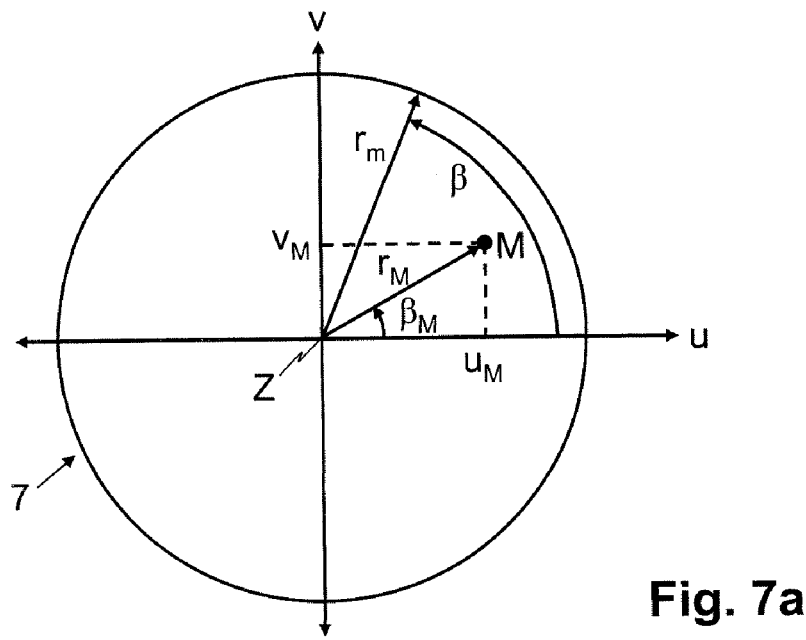
FIG. 7a shows a diagrammatic view of a two-dimensional reference pattern.

The reference pattern generator 31 is set up to generate the two-dimensional reference patterns 7 via the reference pattern projector 32 by modulation of one or more physical optical parameters, in particular by modulation of the light intensity, the light polarization and/or the light wavelength (colour). As is illustrated in FIG. 7a, the reference pattern 7 is, for example, circular and has a radius $r_m$. Each pattern point M of the reference pattern 7 is defined by its cartesian coordinates $(u_M, v_M)$ or polar coordinates $(r_M, \beta_M)$. The modulation of the physical optical parameters is performed in the reference pattern 7 in, for example, a radial fashion, that is to say depending on the radius r and/or depending on the (circular) angle $\beta$. The person skilled in the art will understand, in an alternative design variant, that the reference pattern 7 can also be modulated along a plurality of intersecting straight lines or curves, for example a spider web, chessboard or hexagonal pattern. In a further design variant, aside from reference patterns 7 dynamically generated by the reference pattern generator 31 the reference pattern 7 also comprises basic static patterns which the reference pattern generator 31 superimposes on, or lays under, the dynamically generated reference patterns 7, or which are fitted statically on the display screen.

Figure 7B:
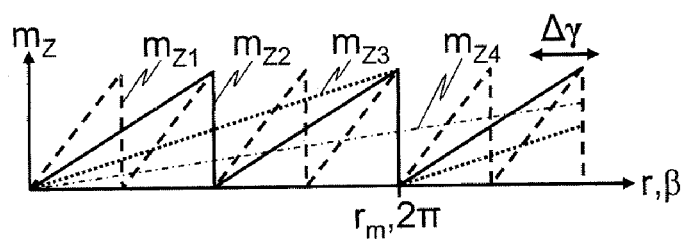
FIG. 7b shows saw tooth modulation profiles for the modulation of a physical optical parameter of the reference pattern.
Figure 7C:
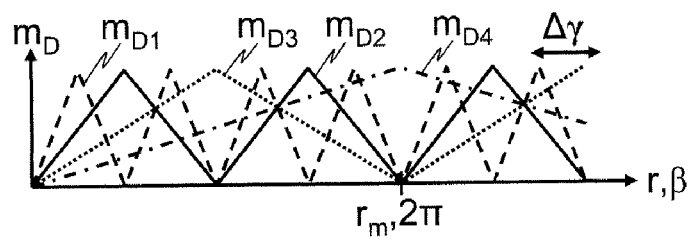
FIG. 7c shows triangular modulation profiles for the modulation of a physical optical parameter of the reference pattern.
Figure 7D:
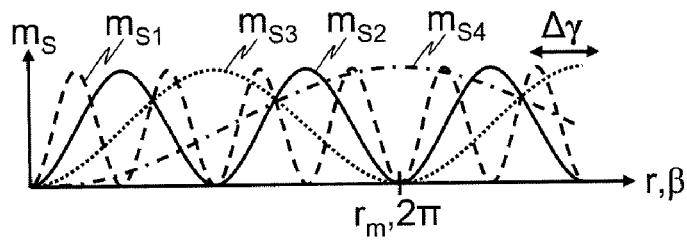
FIG. 7d shows sinusoidal modulation profiles for the modulation of a physical optical parameter of the reference pattern.

FIGS. 7b-7d show different modulation profiles for the modulation of the physical optical parameters of the reference pattern 7. FIG. 7b shows various sawtooth modulation profiles $m_Z$; FIG. 7c shows various triangular modulation profiles $m_D$; and FIG. 7d shows various sinusoidal modulation profiles $m_S$. Here, in order to generate periodic reference patterns 7 the modulation profiles $m_{Z1}$, $m_{Z2}$, $m_{D1}$, $m_{D2}$, $m_{S1}$ and $m_{S2}$ respectively have a period which is multiply repeated over the radius $r=r_m$ or the circular angle $\beta=2\pi$ of the reference pattern 7. The modulation profiles $m_{Z3}$, $m_{D3}$ and $m_{S3}$ respectively have a period which corresponds to the radius $r=r_m$ or the circular angle $\beta=2\pi$ of the reference pattern 7. The modulation profiles $m_{Z4}$, $m_{D4}$ and $m_{S4}$ respectively have a period which is larger than the radius $r=r_m$ or the circular angle $\beta=2\pi$ of the reference pattern 7.

Aside from the modulation profiles $m_Z$, $m_D$ and $m_S$, mentioned, in further design variants the reference pattern generator 31 is also set up to generate other modulation profiles which can be described by Fourier series. In addition, the reference pattern generator 31 is set up to generate the various modulation profiles $m_Z$, $m_D$ and $m_S$ with a phase shift $\Delta\gamma$. The modulation profiles $m_Z$, $m_D$ and $m_S$ define a basic reference pattern which is shifted by the phase shift $\Delta\gamma$ of the modulation profiles $m_Z$, $m_D$ and $m_S$, so it is possible to generate a plurality of mutually phase-shifted reference patterns 7 by phase shifting of a periodic basic reference pattern defined by the modulation profiles $m_Z$, $m_D$ and $m_S$. The reference pattern 7 is preferably formed such that it is possible to generate an identical phase shift $\Delta\gamma$ at every location, the result being the simplification of the processing, since only one evaluation method needs to be applied in the entire image area. A phase shift $\Delta\gamma$ at the point M of the reference pattern 7 has a linear effect on the phase shift $\Delta\gamma'$ in the case of a corresponding pixel B in the reflection image 9. In one design variant, the reference pattern generator 31 is, moreover, set up to vary the period of the various modulation profiles $m_Z$, $m_D$ and $m_S$ during generation of the reference patterns 7, wherein it is possible both for the intensity and for the period to be dependent on location.

The output module 5 comprises one or more output devices, for example a display screen and/or a printer.

The following passages describe the ophthalmological method for measuring the cornea 61, and the functions of the control module 21 and of the reference pattern generator 31, with reference to FIGS. 2-7.

In step S1 of the ophthalmological method, a plurality of reflection images 9 of one or more reflection patterns 8 reflected by the cornea 61 are provided for measuring the cornea 61. To this end, in step S11 one or more different reference patterns 7 are generated by the reference pattern system 3 and projected or emitted onto the cornea 61 by the reference pattern projector 32. In step S12, the image acquisition system 4 acquires one or more reflection patterns 8 which are reflected by the cornea 61 by virtue of the reference patterns 7 generated in step S11. In step S13, different reflection images 9 are stored in the image memory 43 on the basis of the one or the plurality of acquired reflection patterns 8.

In step S2, the processing module 2 determines at least one measured geometrical value of the cornea 61 on the basis of the reflection images 9 stored in step S13. To this end, for points having the coordinates x,y,z on the cornea 61, for example at the reflection point R of the reflection pattern 8, the control module 21 respectively calculates a phase value $\phi$ of the reflection pattern 8 at the relevant point R on the basis of the intensity values which are respectively determined in the stored reflection images 9 at the pixel B corresponding to the relevant point R. The processing module 2 calculates the phase value φ of the reflection pattern 8 at the relevant point R having the coordinates x,y,z, for example by evaluating the equation (1) below:

$$I(x',y') = I_0(x',y')\{1 + sm(x',y')\cos[\phi(x',y')]\} \tag{1}$$

I(x',y') being the measured intensity at the pixel B, having the coordinates x', y', which corresponds to the relevant point R, $I_0$(x',y') being the background intensity at the pixel B, sm(x', y') being a signal modulation (for example attenuation) at the pixel B, and φ(x',y') being the phase value at the pixel B. Here, the phase value φ(x',y') at the pixel B corresponds to the phase value φ(x,y) of the reflection pattern 8 at the relevant reflection point R on the cornea 61. It is therefore necessary to provide at least three independent items of information for the pixel-accurate determination of the phase angle φ and the geometrical measured values based thereon. By determining the intensity I(x',y') for a pixel B (x',y') corresponding to the reflection point R (x,y,z) in a plurality of stored reflection images 9, it is possible to set up a plurality of (for example three) equations for the calculation of the unknown variables background intensity $I_0$(x',y'), signal modulation sm(x',y') and phase value φ(x',y') at the relevant pixel B, and to calculate the phase value φ(x',y') or φ on the basis thereof. The person skilled in the art will understand that other, corresponding equations for the calculation, on the basis of the intensities I(x',y') measured in the stored reflection images 9, of the phase value φ being sought can be set up for nonsinusoidal modulation profiles, for example triangular modulation profiles $m_D$ or sawtooth modulation profiles $m_Z$. When measuring the cornea 61 via the pupil of the eye 6, all that is required is the generation of two reference patterns 7 or the acquisition of two reflection images 9 of the reflection patterns 8 reflected by the cornea 61, since no background light is present in the case of the pupil, and the signal modulation sm(x',y')=1 is constant.

On the basis of the calculated phase values, the processing module 2 determines one or more measured (geometrical) values of the cornea 61, in particular the surface inclination, surface curvature, surface shape (topography) and/or refractive power of the cornea 61. The relationship between the pixel B (x',y') and the pattern point M (u,v) or (r,β) is yielded via the measurement of the phase value φ from the position of the reflection point (x,y,z) on the cornea 61, and the surface normal n at this point (see the triangle defined in FIG. 1 by the points R, O, M). The coordinates x, y can be inferred on the basis of assumptions and/or additional measurements of the distance z of the reflection point R with reference to the coordinate system (x,y,z), positioned at the zero point O, of the measuring instrument 1. The surface inclination can be determined with the aid of the position of the reflection point R (x,y,z). The surface shape is yielded via integration of the surface inclinations at a multiplicity of reflection points R (x,y,z). The more distance values or reflection points R (x,y,z) that are known (often at least the apex), and the more densely the measuring points of the surface inclination lie, and the more accurately the surface inclination can be measured, the more accurately can the surface shape be determined. Surface curvatures can be defined either via derivatives of the surface inclination, or via fitted-in spheres.

In step S3, the measured values determined in step S2 are output to a user by the control module 21 via the output module 5. The output module 5 produces the representation of the measured values determined, such as surface inclination, surface curvature, surface shape (topography) and/or refractive power of the cornea 61 graphically and/or numerically on a display or as a printout.

Figure 2:
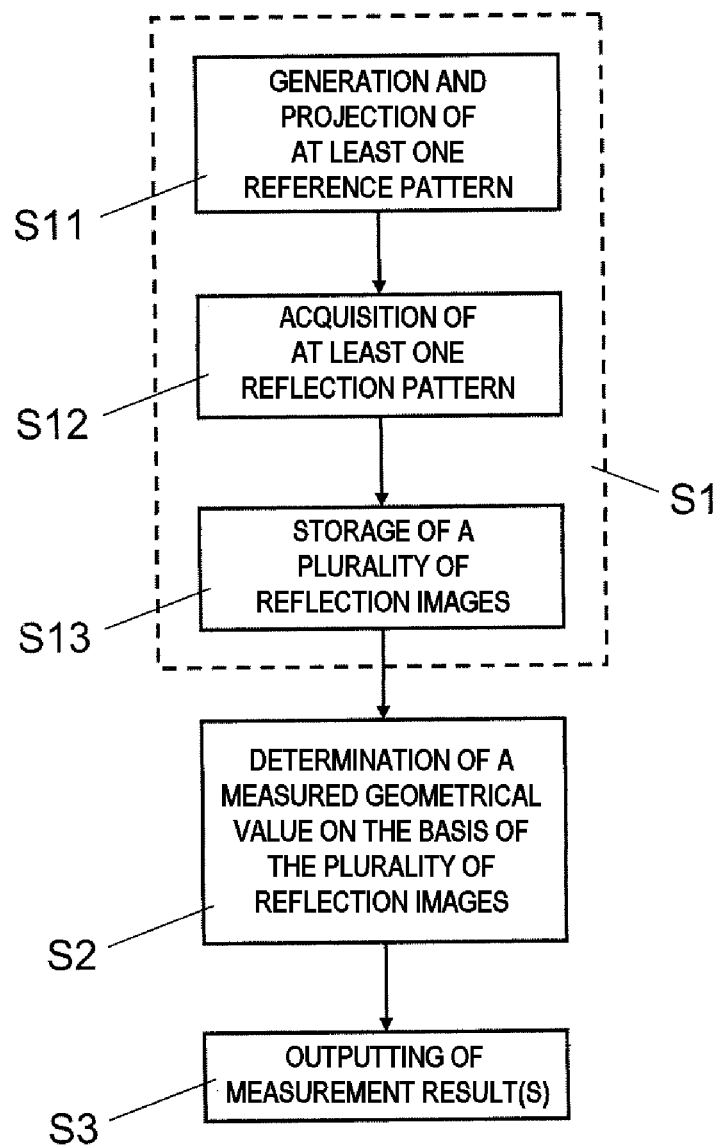
FIG. 2 shows a flowchart which illustrates diagrammatically an exemplary sequence of steps of an ophthalmological method for measuring a cornea.
Figure 3:
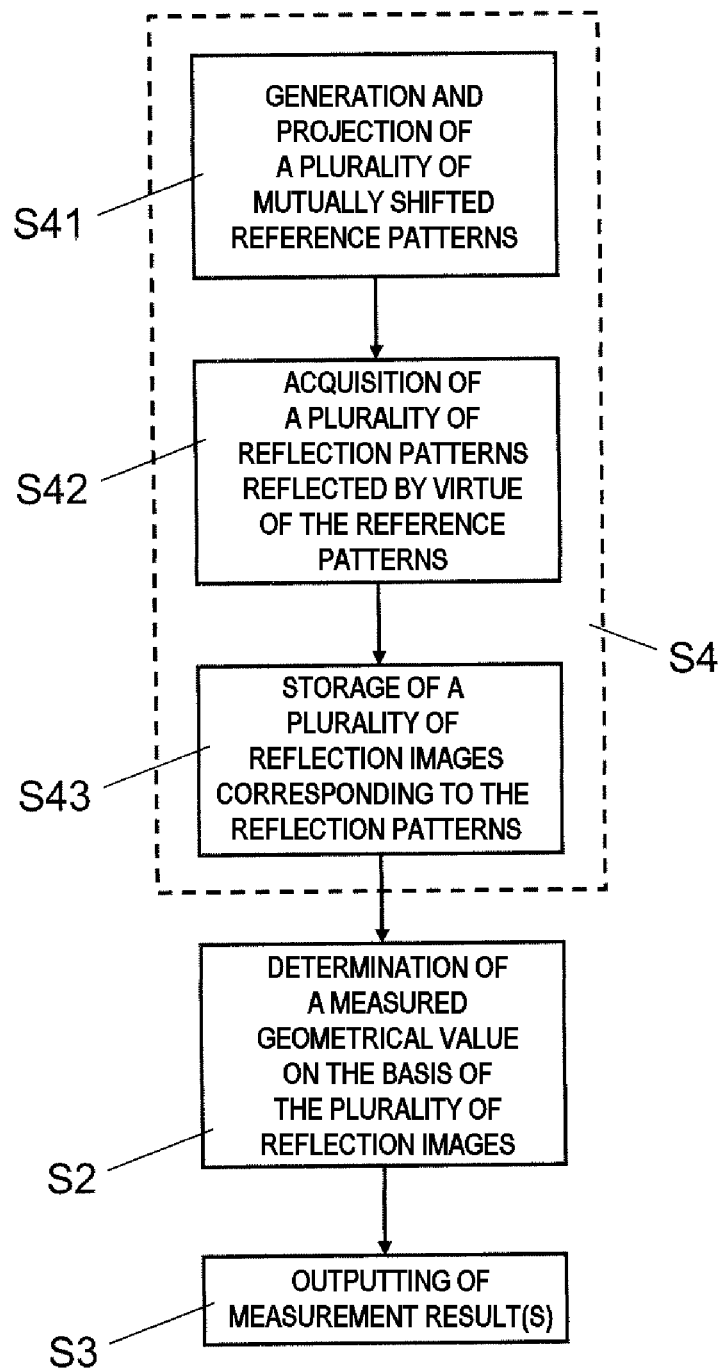
FIGS. 3 to 6 show flowcharts which illustrate diagrammatically various design variants with different sequences of steps of the ophthalmological method for measuring the cornea.

In the design variant in accordance with FIG. 3, the step S1 of the ophthalmological method described above with reference to FIG. 2 is effected by executing the corresponding step S4.

In step S41, the reference pattern system 3 generates a plurality of mutually shifted reference patterns 7 which are projected or emitted onto the cornea 61 by the reference pattern projector 32. To this end, the control module 21 activates the reference pattern generator 31, which generates a plurality of, for example three, mutually phase-shifted reference patterns 7 and projects or emits them onto the cornea 61.

In step S42, the image acquisition system 4 acquires the sequence of the reflection patterns 8, which are reflected by the cornea 61 by virtue of the sequence of reference patterns 7 generated in step S41.

In step S43, the reflection images 9 of the reflection patterns 8 reflected by the cornea 61 are stored in a fashion assigned to one another in the image memory 43. The person skilled in the art will understand that the step sequence is illustrated diagrammatically, and that the sequence of the steps S41, S42, S43 is repeated at least three times, once in each case for the generation of a reference pattern 7 and the acquisition of the reflection pattern 8 or reflection image 9 based thereon.

As described above with reference to FIG. 2, in the subsequent step S2 the processing module 2 determines at least one measured geometrical value of the cornea 61 on the basis of the stored reflection images 9 of the reflection patterns 8. As described above with reference to FIG. 2, in step S3 the measured values determined are output to the user via the output module 5.

It is additionally to be stated at this juncture that in the case of the generation of the three mutually phase-shifted reference patterns 7 in step S41, the result for specific values of the phase shift Δγ is particularly simple equations for the calculation, described with reference to FIG. 2, of the phase value φ on the basis of the intensities $I_1$(x',y'), $I_2$(x',y') and $I_3$(x',y') measured in the stored reflection images 9. For example, the following simple equation is yielded for the phase shift of Δγ=π/2 between the reference patterns 7 (that is to say Δγ$_1$=0, Δγ$_2$=π/2, Δγ$_3$=π):

$$\varphi(x', y') = \arctan\left(\frac{I_1(x', y') - 2I_2(x', y') + I_3(x', y')}{I_1(x', y') - I_3(x', y')}\right) \tag{2}$$

Figure 4:
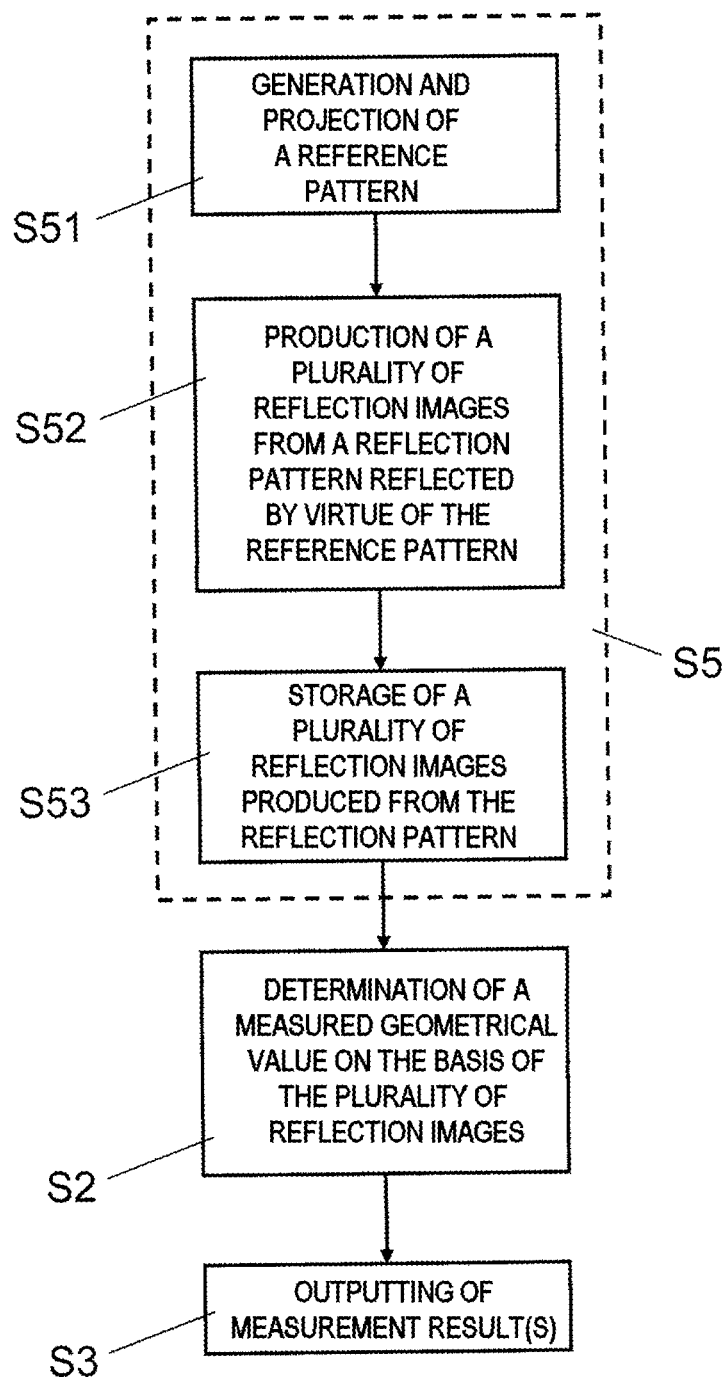

In the design variant in accordance with FIG. 4, the step S1 of the ophthalmological method described above with reference to FIG. 2 is effected by execution of the corresponding step S5.

In step S51, the reference pattern system 3 generates a reference pattern 7 and projects or emits it onto the cornea 61 by means of the reference pattern projector 32. To this end, the control module 21 activates the reference pattern generator 31 which, depending on the design variant, generates the reference pattern 7 with basic reference patterns which have various colours or are differently polarized, that is to say the reference pattern 7 is generated from at least two mutually phase-shifted (periodic) basic reference patterns respectively having different colours or pattern points M of different polarization. The reference pattern 7 is generated, for example, from two basic reference patterns which are mutually phase-shifted by Δγ=π/2)(90° and have different colours (colour channels). In step S51, a plurality of mutually shifted (for example continuous) two-dimensional reference patterns or basic reference patterns having different colours (for example three different colours) or different polarization are projected or emitted simultaneously onto the cornea 61.

In step S52, the image acquisition system 4 acquires the reflection pattern 8, which is reflected by the cornea 61 by virtue of the reference pattern 7 generated in step S51, and stores the reflection pattern 8 in the image memory 43. In step S52, the plurality of reference patterns or basic reference patterns simultaneously projected or emitted in step S51 are therefore acquired. The extraction module 44 is set up to produce a plurality of (at least two) reflection images 9 in step S52 from the stored reflection pattern 8 and store them in a fashion assigned to one another in the image memory 43. As has already been mentioned above, in alternative design variants the extraction module 44 is upstream of the image converter 42 or integrated into the image converter 42 such that the reflection images 9 are not firstly produced on the basis of the stored reflection pattern 8, but are respectively produced without buffer storage of the reflection pattern 8 in a direct optical fashion from the reflection pattern 8 reflected on the cornea 61. Depending on the relevant design variant, the extraction module 44 comprises colour filters for the production of the reflection images 9 by colour filtering from the reflection pattern 8, or polarization filters for the production of the reflection images 9 by polarization filtering from the reflection pattern 8. In order to produce the reflection images 9 by polarization filtering, in one design variant the image acquisition system 4 comprises a plurality of (for example two or three) coaxial optical channels, for example, a plurality of (CCD) cameras which respectively acquire the same reflection pattern 8 by means of differently orientated polarization filters. A polarization measurement based on a plurality of images of different polarization is thereby made possible. The polarization filters can be correspondingly replaced by colour filters and colour filterings. A combination of colour filtering and polarization filtering is also possible.

In step S53, the reflection images 9 produced in step S52 from the reflection pattern 8 are stored in a fashion assigned to one another in the image memory 43.

As described above with reference to FIG. 2, in the following step S2 the processing module 2 determines, on the basis of the reflection images 9 produced, one or more measured geometrical values of the cornea 61 which are output to the user in step S3 via the output module 5.

Figure 5:
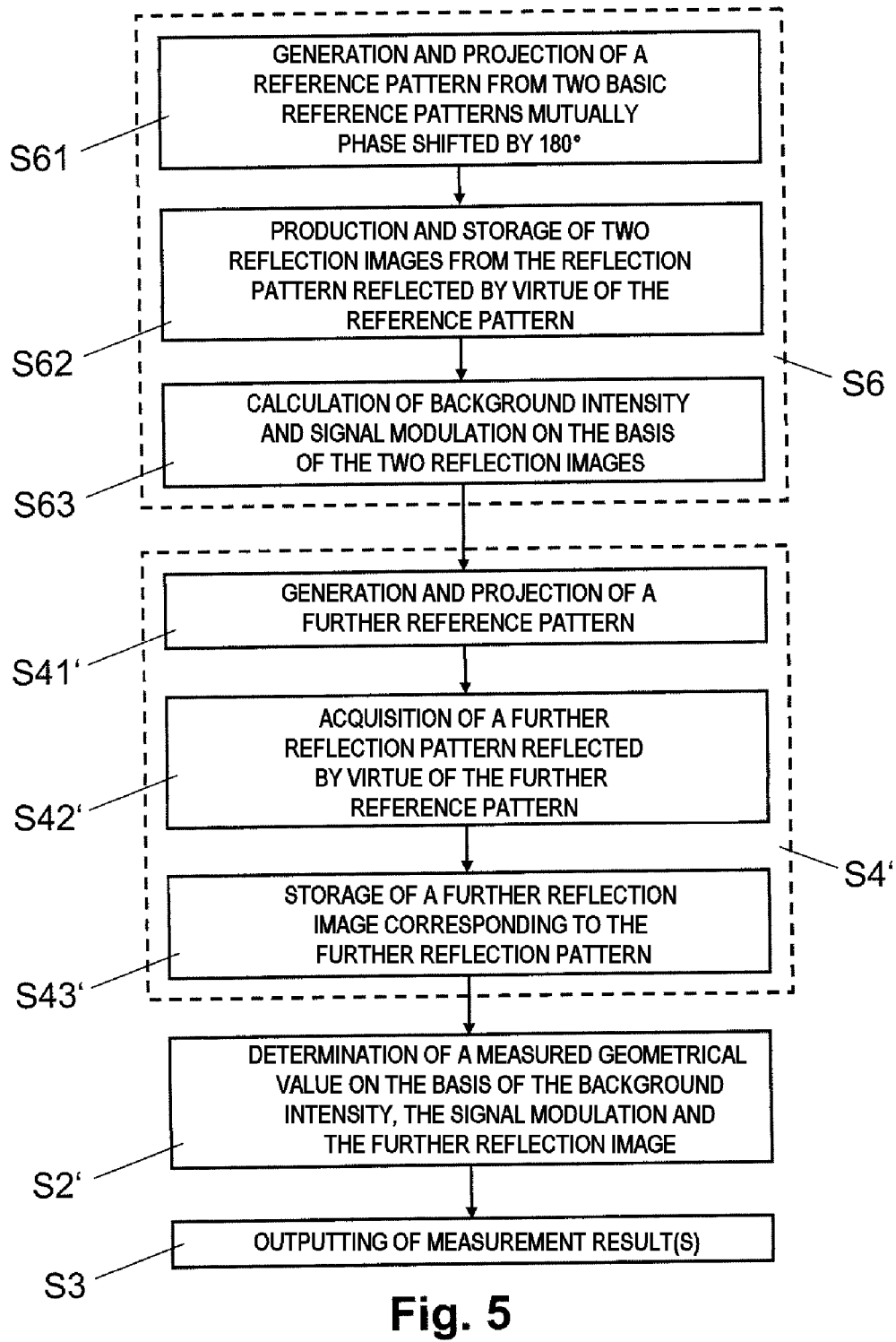
Figure 6:
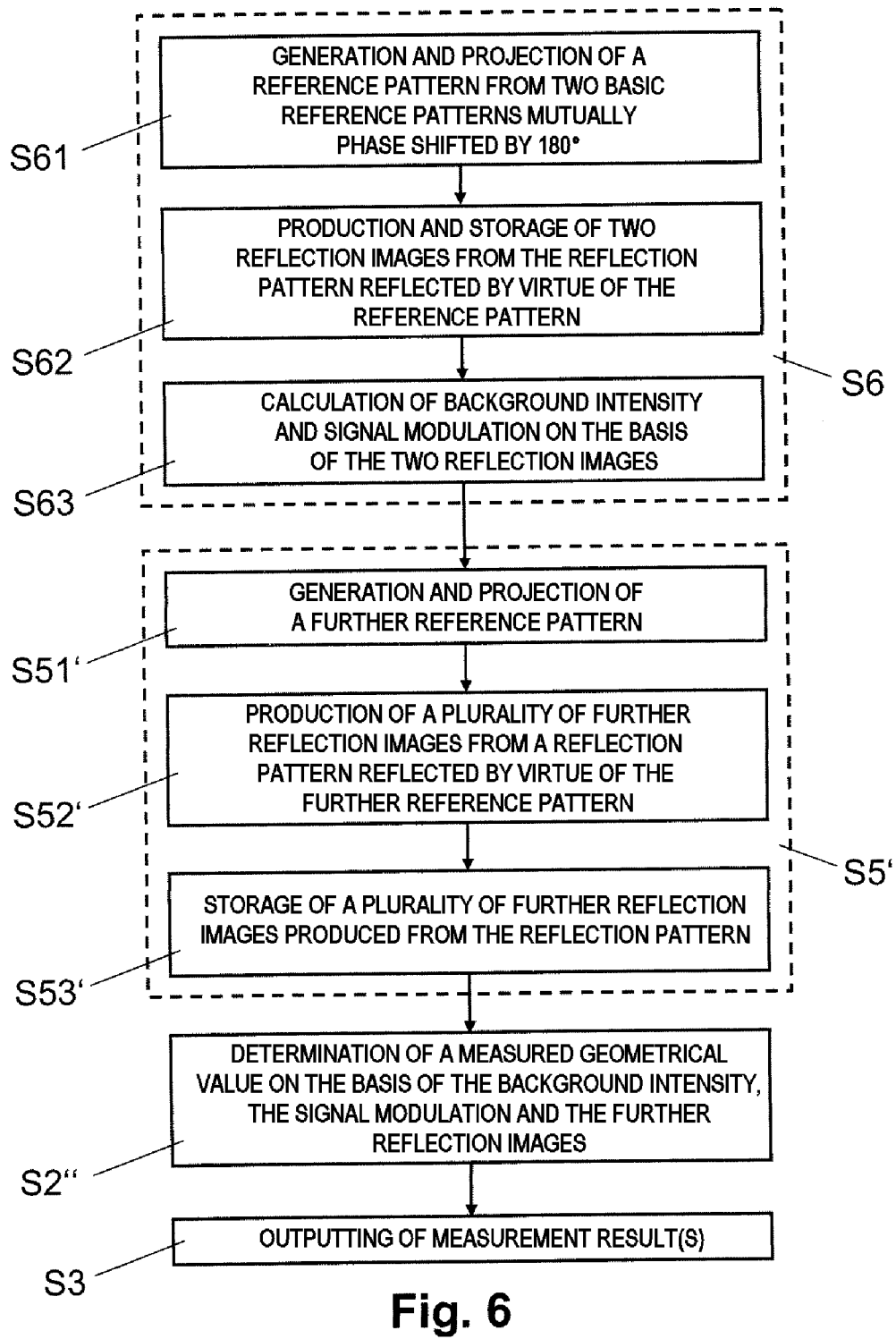

The design variants in accordance with FIGS. 5 and 6 respectively have a step S6 for the separate determination of the background intensity $I_0(x',y')$ at the cornea 61 and of the signal modulation $sm(x',y')$ effected upon the transmission to the cornea 61.

In step S61, the reference pattern system 3 generates a reference pattern 7 from two basic reference patterns mutually shifted by the phase shift $\Delta\gamma=\pi$ (180°) or inverted, and projects or emits it onto the cornea 61 by means of the reference pattern projector 32. As described above with reference to step S51, to this end the control module 21 activates the reference pattern generator 31, which generates the combined reference pattern 7 in dependence on the design variant from two (periodic) basic reference patterns which are mutually phase-shifted by $\Delta\gamma=\pi$ and respectively have a different colour or pattern points M of different polarization.

As described above with reference to step S52, in step S62 the extraction module 44 produces two reflection images 9 and stores them in the image memory 43 in a mutually assigned fashion, this being done on the basis of the reflection pattern 8 which is reflected by the cornea 61 by virtue of the reference pattern 7 generated in step S61.

In step S63, the control module 21 calculates the background intensity $I_0(x',y')$ and the signal modulation $sm(x',y')$ on the basis of the two reflection images 9 acquired in step S62. In this case, the background intensity $I_0(x',y')$ is calculated by addition of the two reflection images 9 and division by the factor two, that is to say in the case of a representation of the reflection images 9 as a matrix of pixels having an intensity value $I(x',y')$, the intensity values $I(x',y')$ of matrix elements of the reflection images 9 with the same indices x', y' are added and divided by two. The signal modulation $sm(x',y')$ is calculated by subtraction of the two reflection images 9 and division by the factor two, that is to say the intensity values $I(x',y')$ of the matrix elements with the same indices x', y' are subtracted and divided by two and, if appropriate, weighted with a further factor for the subsequent processing. In the case of binary reference patterns 7, the calculated signal modulation $sm(x',y')$ is present as a numerical value. In the case of continuous reference patterns 7, the subtraction of two intensity values $I_1(x',y')$ and $I_2(x',y')$ of a relevant point (x',y') for the signal modulation $sm(x',y')$ results in the expression below for the case of sinusoidal modulation profiles:

$$I_1(x',y')-I_2(x',y')=2I_0(x',y')sm(x',y')\cos(\phi(x',y')), \quad (3)$$

the background intensity $I_0(x',y')$ being known from the addition of the two reflection images 9, and the phase value $\phi$ having to be calculated in a subsequent step, as is described below with reference to FIGS. 5 and 6.

In accordance with the design variant according to FIG. 5, in step S4' a further reference pattern 7 is used for the evaluation of equation (1). In step S41', a further reference pattern 7 is generated by the reference pattern system 3 or by the reference pattern generator 31, and is projected or emitted onto the cornea 61 by the reference pattern projector 32. The further reference pattern 7 generated in step S41' preferably has a mean intensity which corresponds to the mean intensity of the two reference patterns 7 mutually phase-shifted by $\Delta\gamma=\pi$ (180° in step S61. In a variant of the two reference patterns generated in step S61, the further reference pattern 7 has, for example, a phase shift of $\Delta\gamma=\pi/2$ (90°).

In step S42', the image acquisition system 4 acquires the further reflection pattern 8, which is reflected by the cornea 61 by virtue of the further reference pattern 7.

In step S43', the reflection image 9 of the further reflection pattern 8 reflected by the cornea 61 is stored in the image memory 43 in a fashion assigned to the background intensity $I_0(x',y')$ and signal modulation $sm(x',y')$ calculated in step S6.

In step S2', the processing module 2 or the control module 21 respectively determines for points R having the coordinates (x,y,z) on the cornea 61 in each case a phase value $\phi$ of the further reflection pattern 8 in accordance with equation (1) in the case of sinusoidal reference patterns 7 (that is to say reference patterns 7 with sinusoidal modulation profiles), on the basis of the background intensity $I_0(x',y')$ and signal modulation $sm(x',y')$ calculated in step S6, as well as on the basis of the intensity value $I(x',y')$ which is determined in the stored reflection image 9 at the corresponding pixel B, account also being taken of the phase shift $\Delta\gamma$ of the further reference pattern 7 in dependence on the design variant. When binary reference patterns 7 are used in step S6, the numerical value of the calculated signal modulation $sm(x',y')$ is substituted in equation (1) in order to calculate the phase value $\phi$. When continuous sinusoidal reference patterns 7 are used in step S6, the phase value $\phi$ is calculated by solving the two equations (1) and (3). As has been described above with reference to FIG. 2, the processing module 2 determines one or more measured (geometrical) values of the cornea 61 on the basis of the calculated phase value φ. Analogous equations must be used in the case of reference patterns of other shapes.

As described above with reference to FIG. 2, in step S3 the measured values determined are output to the user via the output module 5.

In accordance with the design variant according to FIG. 6, a further reference pattern 7 is used in step S5' in order to evaluate equation (1).

In step S51', the reference pattern system 3 or reference pattern generator 31 generates a further reference pattern 7 and projects or emits it onto the cornea 61 is in the reference pattern projector 32. The further reference pattern 7 generated in step S51' preferably has a mean intensity which corresponds to the mean intensity of the two reference patterns 7 generated in step S61 and shifted with respect to one another by $\Delta\gamma=\pi$ (180°). As has been described above with reference to FIG. 4, the further reference pattern 7 is generated in dependence on the design variant with basic reference patterns which have various colours and/or are differently polarized.

In the design variant with basic reference patterns which have various colours and are, for example, phase-shifted by $\Delta\gamma=\pi/2$ (90°), the background intensity $I_0(x',y')$ and signal modulation $sm(x',y')$ determined in step S6 are respectively determined for the two colour channels which are used (that is to say for the basic reference patterns of the two colours used).

In step S52', the image acquisition system 4 acquires the reflection pattern 8 which is reflected by the cornea 61 by virtue of the reference pattern 7 generated in step S51' and, as has been described above with reference to FIG. 4, the extraction module 44 produces a plurality of further reflection images 9 from the acquired reflection pattern 8 by colour filtering or polarization filtering from the reflection pattern 8.

In step S53', the further reflection images 9 produced are stored in the image memory 43 in a fashion assigned to the background intensity $I_0(x',y')$ and signal modulation $sm(x',y')$ calculated in step S6, possible eye movements being taken into account in the assigned storage.

In step S2'', the control module 21 respectively determines, for points R having the coordinates (x,y,z) on the cornea 61, the phase value φ of the reflection pattern 8, doing so on the basis of the background intensity $I_0(x',y')$ and signal modulation $sm(x',y')$ calculated in step S6 as well as the intensity values $I(x',y')$ which are determined in the stored reflection images 9 at the corresponding pixel. When binary reference patterns 7 are used in step S6, the numerical value of the calculated signal modulation $sm(x',y')$ is substituted in equation (1) in order to calculate the phase value φ. When continuous sinusoidal reference patterns 7 are used in step S6, the phase value φ is calculated by solving the two equations (1) and (3). Since equation (1) corresponds to the plurality of stored reflection images 9, a separate phase value $\phi_i(x',y')$ is respectively determined for the reflection images 9 and there is calculated therefrom, by averaging, a resulting phase value $\phi(x',y')$ which averages out measurement inaccuracies in the determination of the separate phase values $\phi_i(x',y')$. The processing module 2 determines one or more measured (geometrical) values of the cornea 61 on the basis of the calculated phase value $\phi(x',y')$ and, as described above with reference to FIG. 2, in step S3 the measured values determined are output to the user via the output module 5.

An advantage of the method illustrated in FIGS. 5 and 6 is the reduced number of images which are to be acquired simultaneously. In the case of the use of three CCD cameras, it is therefore possible to save one camera and the optical elements associated therewith.

It may be stated in conclusion that in order to improve the measuring accuracy in further design variants, the ophthalmological device 1 comprises fixing targets, devices for measuring the distance between the eyes, eye trackers and/or means for acquiring and evaluating overdetermined measured data, that is to say more than the minimally required number of reference images 9.

It may be explicitly maintained once again that, although the use of continuous patterns increases the number of measuring points, it is only through the use of a plurality of images that the measuring accuracy is increased owing to the elimination of the background illumination and owing to account being taken of the signal modulation. Furthermore, the use of a plurality of images enables the additional calculation of Q values for testing the measuring accuracy. The additional calculation of the signal modulation indicates the signal-to-noise ratios, and thus the measurement uncertainty. A calculation of the phase shift angle points to eye movements. The Q parameters can be used to adapt the reference pattern (for example in the case of too tightly packed strips owing to excessively tightly packed periods in the reflected reflection pattern) to the eye that is to be measured.

Finally, it may be stated here that although in the description computer program code was assigned to specific functional modules, and the execution of steps was represented in a specific sequence, the person skilled in the art will nevertheless understand that the computer program code can be differently structured, and the sequence of at least certain steps can be changed, without deviating thereby from the subject of protection.

What is claimed is:

1. Ophthalmological method for measuring a cornea, comprising:
    projecting the two-dimensional reference pattern onto the cornea;
    acquiring a reflection pattern reflected by the cornea by virtue of the reference pattern;
    storing a plurality of different reflection images of one or more reflection patterns reflected by the cornea by virtue of the phase-shifted reference patterns;
    measuring intensities in the plurality of different reflection images at a pixel corresponding to a point on the cornea;
    calculating for the point on the cornea a phase value of the reflection pattern on the basis of the intensities measured in the plurality of different reflection images by evaluating the equation $$I(x',y')=I_0(x',y')\{1+m(x',y')\cos[\phi(x',y')]\},$$

$I(x',y')$ being a measured intensity at the corresponding pixel with coordinates x',y', $I_0(x',y')$ being a background intensity at the pixel, $m(x',y')$ being a signal modulation at the pixel, and $\phi(x',y')$ being the phase value at the relevant point, and determining at least one measured geometerical value of the cornea on the basis of the phase value.
    determining at least one measured geometrical value of the cornea on the basis of the phase value.

2. Ophthalmological device for measuring a cornea, comprising:
    a reference pattern system for the projection of a two-dimensional reference pattern onto the cornea;
    an image acquisition system for acquiring a reflection pattern reflected by the cornea by virtue of the reference pattern,
    wherein the image acquisition system is set up to store a plurality of different reflection images of one or more reflection patterns reflected by the cornea; and the device comprises a processing module which is set up to determine at least one measured geometrical value of the cornea on the basis of the plurality of different reflection images stored, wherein the processing module is set up to respectively calculate a phase value of the reflection pattern for points on the cornea, doing so on the basis of intensities respectively measured in the stored reflection images at a pixel corresponding to the relevant point, by evaluating the equation $$I(x',y') = I_0(x',y')\{1 + m(x',y')\cos[\phi(x',y')]\},$$

$I(x', y')$ being a measured intensity at the corresponding pixel with coordinates $x'$, $y'$, $I_0(x', y')$ being a background intensity at the pixel, $m(x', y')$ being a signal modulation at the pixel, and $\phi(x', y')$ being the phase value at the relevant point, and determine at least one measured geometrical value of the cornea on the basis of the phase value.

* * * * *